United States Patent
Richmond

(10) Patent No.: US 7,552,061 B2
(45) Date of Patent: Jun. 23, 2009

(54) METHOD AND SYSTEM FOR PROVIDING PRESCRIPTION DRUG COVERAGE

(76) Inventor: Gregory Richmond, 3886 Peabody Dr., Bloomfield Hills, MI (US) 48302

( * ) Notice: Subject to any disclaimer, the term of this patent is extended or adjusted under 35 U.S.C. 154(b) by 1733 days.

(21) Appl. No.: 09/799,072

(22) Filed: Mar. 6, 2001

(65) Prior Publication Data

US 2002/0128863 A1  Sep. 12, 2002

(51) Int. Cl.
 *G06Q 50/00* (2006.01)
(52) U.S. Cl. .................... 705/2; 705/3; 705/4
(58) Field of Classification Search ............ 705/2, 705/3, 4
 See application file for complete search history.

(56) References Cited

U.S. PATENT DOCUMENTS

| | | | | |
|---|---|---|---|---|
| 4,491,725 | A | | 1/1985 | Pritchard ...................... 705/2 |
| 4,858,121 | A | | 8/1989 | Barber et al. .................. 705/2 |
| 4,987,538 | A | | 1/1991 | Johnson et al. ................ 705/2 |
| 5,070,452 | A | | 12/1991 | Doyle, Jr. et al. .............. 705/2 |
| 5,235,507 | A | | 8/1993 | Sackler et al. ................ 705/2 |
| 5,359,509 | A | | 10/1994 | Little et al. .................... 705/2 |
| 5,583,760 | A | | 12/1996 | Klesse ......................... 705/38 |
| 5,644,778 | A | | 7/1997 | Burks et al. .................. 705/2 |
| 5,696,906 | A | | 12/1997 | Peters et al. ................ 705/34 |
| 5,715,397 | A | | 2/1998 | Ogawa et al. ............... 709/24 |
| 5,790,548 | A | | 8/1998 | Sistanizadeh et al. ....... 370/401 |
| 5,819,228 | A | | 10/1998 | Spiro .......................... 705/2 |
| 5,832,460 | A | | 11/1998 | Bednar et al. ................ 705/27 |
| 5,832,488 | A | * | 11/1998 | Eberhardt ................... 707/10 |
| 5,852,812 | A | | 12/1998 | Reeder ....................... 705/39 |
| 5,882,192 | A | * | 3/1999 | Bergersen .................... 433/2 |
| 5,884,271 | A | * | 3/1999 | Pitroda ....................... 705/1 |
| 5,884,284 | A | | 3/1999 | Peters et al. ................ 705/30 |
| 5,920,847 | A | | 7/1999 | Kolling et al. .............. 705/40 |
| 5,924,074 | A | | 7/1999 | Evans ......................... 705/3 |
| 5,933,809 | A | | 8/1999 | Hunt et al. .................. 705/3 |
| 6,012,035 | A | | 1/2000 | Freeman, Jr. et al. ........ 705/2 |
| 6,023,684 | A | | 2/2000 | Pearson ...................... 705/35 |

(Continued)

FOREIGN PATENT DOCUMENTS

EP  0 491 497  6/1992

OTHER PUBLICATIONS

"The future of card technology in health care", Kelly, Beckie, Health Data Management, v10, n5, p. 64, May 2002, Dialog File 13, Acc. No. 1252858.*

(Continued)

*Primary Examiner*—Gerald J. O'Connor
*Assistant Examiner*—R. David Rines
(74) *Attorney, Agent, or Firm*—Hunton & Williams, LLP

(57) ABSTRACT

The present invention provides a method and system for enabling an employer or other entity the ability to provide prescription drug coverage efficiently and cost effectively. A card (or other object) may enable access to a general account established by a plan sponsor (e.g., an employer) where the plan sponsor may pay for the pharmacy benefits. As the card is used for the purchase of prescription drugs (or other authorized use), the plan sponsor's general account balance may be reduced. According to another embodiment of the present invention, the card may be restricted for use at selected merchants and may be coded for one or more specific uses, such as obtaining prescription drugs. Other restrictions may be specified for other venues and/or other uses.

14 Claims, 4 Drawing Sheets

U.S. PATENT DOCUMENTS

| | | | |
|---|---|---|---|
| 6,052,674 A | 4/2000 | Zervides et al. | 705/40 |
| 6,065,675 A * | 5/2000 | Teicher | 235/380 |
| 6,088,677 A | 7/2000 | Spurgeon | 705/4 |
| 6,092,055 A | 7/2000 | Owens et al. | 705/34 |
| 6,112,183 A | 8/2000 | Swanson et al. | 705/2 |
| 6,195,612 B1 * | 2/2001 | Pack-Harris | 702/2 |
| 6,208,973 B1 * | 3/2001 | Boyer et al. | 705/2 |
| 6,223,213 B1 | 4/2001 | Cleron et al. | 709/20 |
| 6,341,265 B1 | 1/2002 | Provost et al. | 705/4 |
| 6,343,271 B1 | 1/2002 | Peterson et al. | 705/4 |
| 6,374,229 B1 | 4/2002 | Lowrey et al. | 705/34 |
| 6,393,404 B2 | 5/2002 | Waters et al. | 705/2 |
| 6,453,297 B1 | 9/2002 | Burks et al. | 705/3 |
| 6,988,075 B1 * | 1/2006 | Hacker | 705/3 |
| 2001/0034618 A1 | 10/2001 | Kessler et al. | 705/4 |
| 2002/0002495 A1 * | 1/2002 | Ullman | 705/21 |
| 2002/0007290 A1 * | 1/2002 | Gottlieb | 705/4 |
| 2002/0010594 A1 | 1/2002 | Levine | 705/2 |
| 2002/0019749 A1 | 2/2002 | Becker et al. | 705/2 |
| 2002/0035484 A1 * | 3/2002 | McCormick | 705/2 |
| 2002/0035529 A1 * | 3/2002 | Tooke, III | 705/35 |
| 2002/0049617 A1 * | 4/2002 | Lencki et al. | 705/4 |
| 2002/0062224 A1 | 5/2002 | Thorsen et al. | 705/4 |
| 2002/0082863 A1 | 6/2002 | Kleinke | 705/2 |
| 2002/0120466 A1 | 8/2002 | Finn | 705/2 |
| 2002/0128879 A1 * | 9/2002 | Spears | 705/4 |
| 2002/0152097 A1 * | 10/2002 | Javors | 705/2 |

OTHER PUBLICATIONS

Communications News, Mar. 1999, vol. 36, Issue 3, p. 48.
Citrix Customer Profiles: Wyland Galleries Hawaii, pp. 1-3, date unknown.
Citrix Press Release: HealthPoint Licenses Citrix WinFrame Thin-Client/Server Software, Jun. 30, 1997, pp. 1-3.
Traeden, Jason, Standardize and upgrade mixed computing environment, Health Management Technology, vol. 20, No. 10, pp. 24-26, Nov. 1999.

* cited by examiner

METHOD AND SYSTEM FOR PROVIDING PRESCRIPTION DRUG COVERAGE

FIELD OF INVENTION

The present invention relates generally to the field of providing health care coverage, in particular, to a method and system for enabling payment through a general account associated with an employer or other entity to provide immediate payment of health care services or products (e.g., prescriptions) and reduce overhead costs.

BACKGROUND OF THE INVENTION

Traditionally, customers present a prescription for a drug or other medication to a pharmacy. Customers may be covered by a health care insurance company or other provider through an employer or other entity. At the point of sale, the customer pays a co-pay amount, if applicable, and receives the requested prescription. The pharmacy, on the other hand, may have to wait approximately 45 days or longer to receive payment for the prescription given to the customer.

Currently, employers who offer a prescription drug benefit program may incur large amounts of administration and other related costs. For example, numerous administrative entities may need to approve each stage of a payment process for a prescription. Patient and physician information may need to be verified before payment is rendered. Also, insurance providers may need to be consulted before finally completing the payment process. Generally, the prescription drug transaction is inefficient and requires a large amount of various administrative functions. Patients are generally addressed on an individual basis through individual accounts. Due to the large amount of processing and administrative functions, there may be greater opportunities for errors. As a result, payment to pharmacies and affiliated merchants may be delayed by days, weeks or even longer. In addition, insurance companies and/or other agents may charge numerous fees from the employer thereby contributing to the high costs of prescription drugs and other related services.

These and other drawbacks exist with current systems.

SUMMARY OF THE INVENTION

Additional advantages of the invention will be set forth in part in the description which follows, and in part will be understood from the description, or may be learned by practice of the invention. The embodiments and advantages of the invention may be realized and attained by means of the instrumentalities and combinations particularly pointed out in the appended claims.

The present invention provides a method and system for enabling an employer or other entity the ability to provide health care coverage, in particular, prescription drug coverage, efficiently and cost effectively. A user may present a card (or other object) at the time of purchase. The card may authorize immediate payment through a general account established by a plan sponsor (e.g., an employer) where the plan sponsor may be responsible for payment for the pharmacy benefits. As the card is used for the purchase of health care services (e.g., prescription drugs or other authorized use), the plan sponsor's general account balance may be reduced by the amount charged or other agreed amount.

According to another embodiment of the present invention, the object (e.g., a card) may be defined as being valid for one or more specific merchant venues (e.g., retail stores, merchant chains, etc.). In addition, the object (e.g., a card) may be restricted to one or more uses (e.g., health care benefits, prescriptions, etc.). For example, a prescription card of the present invention may be restricted for use at one or more selected pharmacies and may be coded for the use in obtaining prescription drugs. Other restrictions may be specified for other venues and/or other uses.

The accompanying drawings, which are incorporated in and constitute a part of this specification, illustrate various embodiments of the invention and, together with the description, serve to explain the principles of the invention.

DETAILED DESCRIPTION OF THE PREFERRED EMBODIMENTS

The present invention may enable an employer or other entity the ability to provide prescription drug coverage in a cost efficient manner. According to an embodiment of the present invention, an object, such as a card, may be defined as being valid at a specific merchant, chain of merchants, or other defined groups of merchants. In addition, one or more valid uses may be identified, which may include health care products and/or services, such as prescriptions. For example, a prescription card of the present invention may be valid at one or more selected pharmacies and may be valid for obtaining prescription drugs. Other merchant channels and/or uses may be specified.

According to another embodiment of the present invention, a specific merchant may be selected to establish a private label venue. For example, the private label venue may enable a particular merchant to restrict the use of the card to the specific merchant. Other merchant specifics may be identified, such as location, store affiliation and other defined characteristics and factors. For example, a prescription card may be coded to be valid at a single merchant. In this example, the prescription card (or other object) may bear a logo (or other identifying mark, slogan, etc.) associated with the single merchant that the card has been restricted to.

A customer (or user) may submit a prescription card of the present invention with a prescription issued by a physician (or other authorized entity) to a pharmacy associated with an authorized merchant. The pharmacist may fill the order and collect a co-pay, as indicated on the front of the prescription card (or other object), for example. The prescription card may then be swiped with the cardholder's signature completing the transaction. At this point, the plan sponsor's general account balance may be reduced by the amount of the transaction. The present invention may be used via various communication media, such as mail order, Internet and others.

According to another embodiment of the present invention, a pharmacy benefit manager may be implemented to enable a cardholder to obtain medications safely, conveniently and less expensively. Other services may be offered as well.

Figure 1:
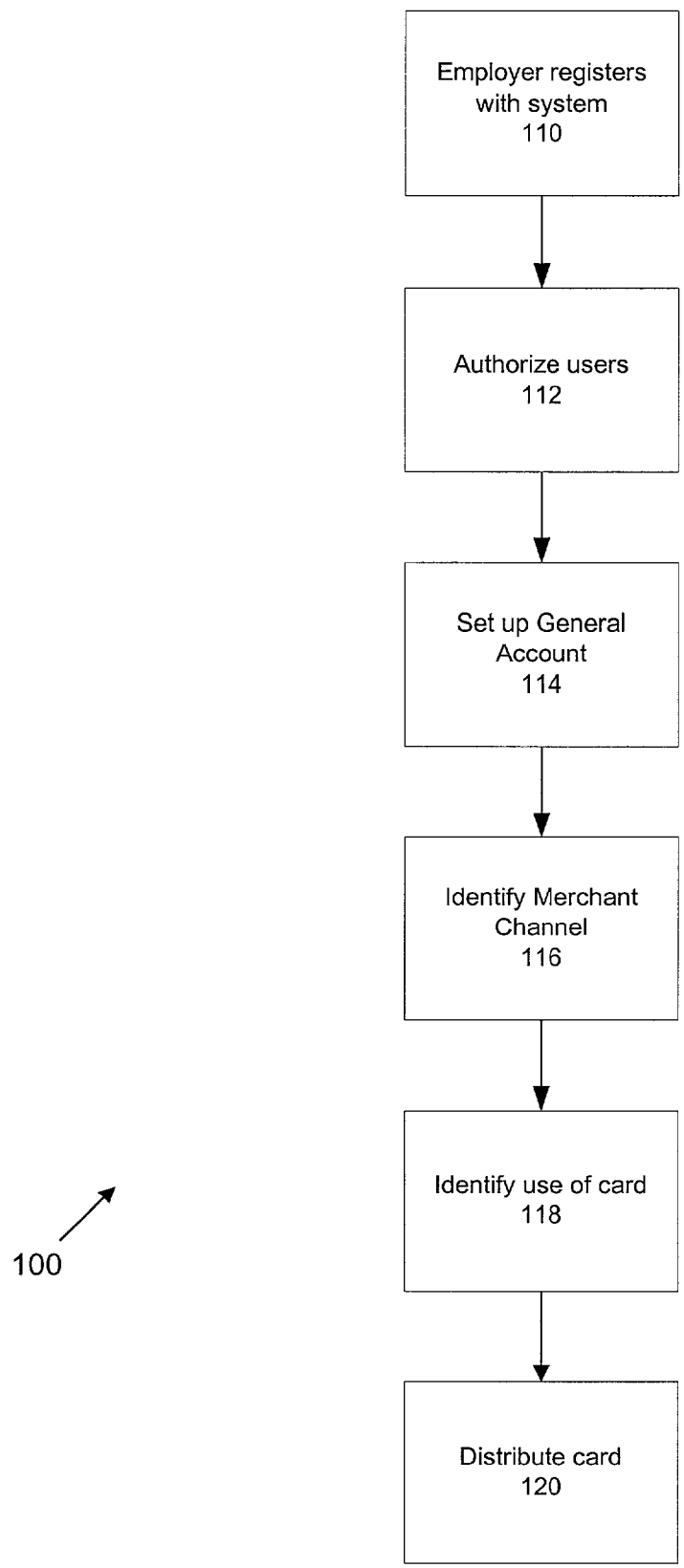
FIG. 1 is a flowchart illustrating a process for providing prescription drug coverage, according to an embodiment of the present invention.

FIG. 1 is an example of a flowchart 100 illustrating a process for providing health care coverage (e.g., prescription drug coverage) in accordance with the present invention. At step 110, an employer or other entity may register with a system of the present invention. At step 112, the employer or other entity may authorize a group of users, such as employees and other individuals. At step 114, a general account associated with the employer may be initiated. At step 116, one or more retail/merchant channels may be identified. At step 118, one or more uses of a card (or other object associated with the system) may be identified. At step 120, the card may be distributed to each authorized user.

Steps of the process will be described in more detail below. While the examples have generally pertained to prescription drug coverage applications, the method and system of the present invention may be applied to other areas as well. The scope of the present invention is not limited to health care programs providing prescription drug coverage.

At step 110, an employer or other entity may register with a system of the present invention. Registration may occur through the Internet, telephone, mail, in person or other mode of communication. An employer or other entity may include government entities (e.g., local, state, etc.), unions, associations, and private and public companies, for example. Registration information, such as payment, location, affiliation, and other information, may be gathered from the employer or other entity at this step.

At step 112, the employer may identify employees or other potential users who may participate in the system of the present invention. Users may include individuals indicated as being eligible to receive health coverage from the employer. Levels of authorization, degrees of benefit, types of coverage, payment information and other data may also be provided for each user or group of users.

At step 114, the employer or other entity may establish a general account from which payments may be made for transactions associated with the identified employees or other potential users. The general account enables users associated with an employer (or other entity) to be handled in a collective fashion, rather than an individual account basis, thereby promoting efficiency and simplicity. As a result, less processing may be involved.

At step 116, a merchant channel may be identified. For example, a prescription object (which may include a card) may be valid for a defined scope of available merchants. This feature of the present invention may limit the prescription object's validity to a single merchant, chain of merchants or other specified group of merchants. This enables a particular merchant the ability to enhance the flow of customers and promote exclusivity. According to another embodiment of the present invention, a merchant's logo or other identifying character or mark may be affixed to the prescription object (e.g., a card) thereby affiliating the prescription object and benefits therein with a specific merchant (or other provider).

At step 118, one or more types of use may be identified. According to an embodiment of the present invention, an associated object (e.g., a card) may be restricted to obtaining health care benefits. More specifically, the card may be restricted to purchasing prescriptions. Other use restrictions may be specified. For example, certain types of prescriptions may be restricted out of use with a prescription card of the present invention. For example, the use of a prescription card to purchase medications for cosmetic purposes may be restricted. Other use restrictions may apply, for example, to weight loss drugs.

At step 120, the card or other associated object may be distributed to each authorized user associated with the employer. The card, for example, may be presented to a merchant at the time of purchase. An account number imprinted on the card may be used for online transactions, mail orders or other types of purchases.

Figure 2:
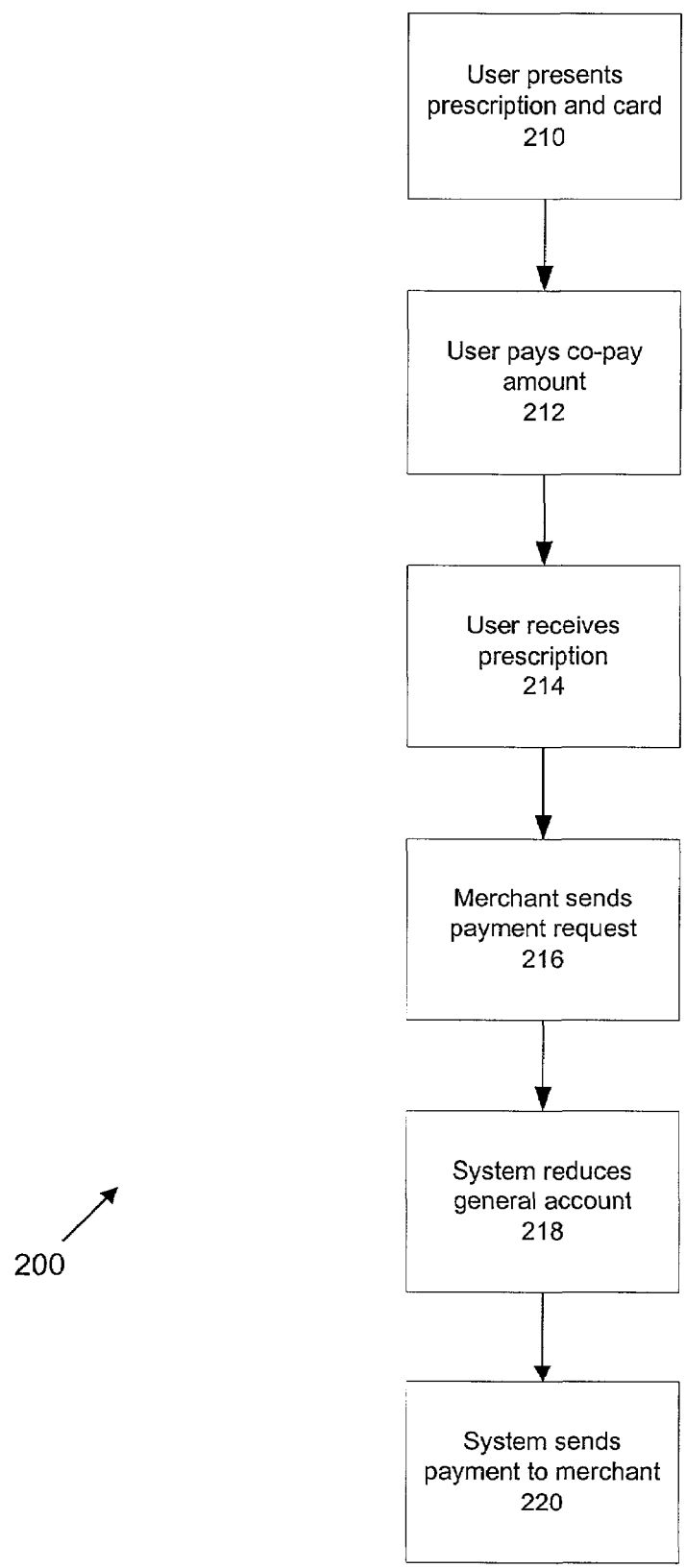
FIG. 2 is a flowchart illustrating a process for receiving prescription drug coverage, according to an embodiment of the present invention.

FIG. 2 is an example of a flowchart 200 illustrating a process for receiving health care coverage (e.g., prescription drug coverage) in accordance with the present invention. At step 210, an authorized user may present a card, for example, with a prescription to an authorized merchant. At step 212, a user may pay a co-pay amount, if applicable. At step 214, a user may receive the requested medication or drugs from the authorized merchant. At step 216, the authorized merchant may forward a payment request. At step 218, the system of the present invention may fulfill the payment request by reducing the general account by a corresponding amount. At step 220, the payment may then be sent to the authorized merchant thereby fulfilling the payment request.

Steps of the process will be described in more detail below. While the examples have generally pertained to prescription drug coverage applications, the method and system of the present invention may be applied to other areas as well. The scope of the present invention is not limited to health care programs providing prescription drug coverage.

At step 210, a user may present a prescription card (or other object) with a prescription issued by a physician or other authorized entity to a pharmacy where the pharmacy may be associated with the identified merchant channel.

At step 212, the pharmacist may collect a co-pay, if applicable. The co-pay may generally be displayed on the prescription card, for example. At step 214, the user may receive the requested medication or drugs. The dispensing of the requested products may be subject to various restrictions, such as merchant channel, use, or other restrictions which may be imprinted on the card itself or encoded into the card.

At step 216, a merchant may send a payment request to a system of the present invention. This may occur when a prescription card is accessed by an authorized merchant. For example, a prescription card may be swiped with the customer's signature completing the transaction. When this occurs, a payment request from an identified merchant may be forwarded. The payment request may be for a transaction amount reduced by the co-pay amount received from the user.

At step 218, the system of the present invention may reduce the general account associated with an employer of the user by the amount of the payment request.

As prescriptions are being fulfilled by a pharmacy entity associated with the authorized merchant for a proper authorized use, the merchant may receive immediate payment for the prescription through the general account associated with the employer (or other entity) of the customer, at step 220. The employer may pay for the pharmacy benefits so that as the prescription object is being used for the purchase of prescription drugs, the employer's general account balance may be reduced by a corresponding amount.

Figure 3:
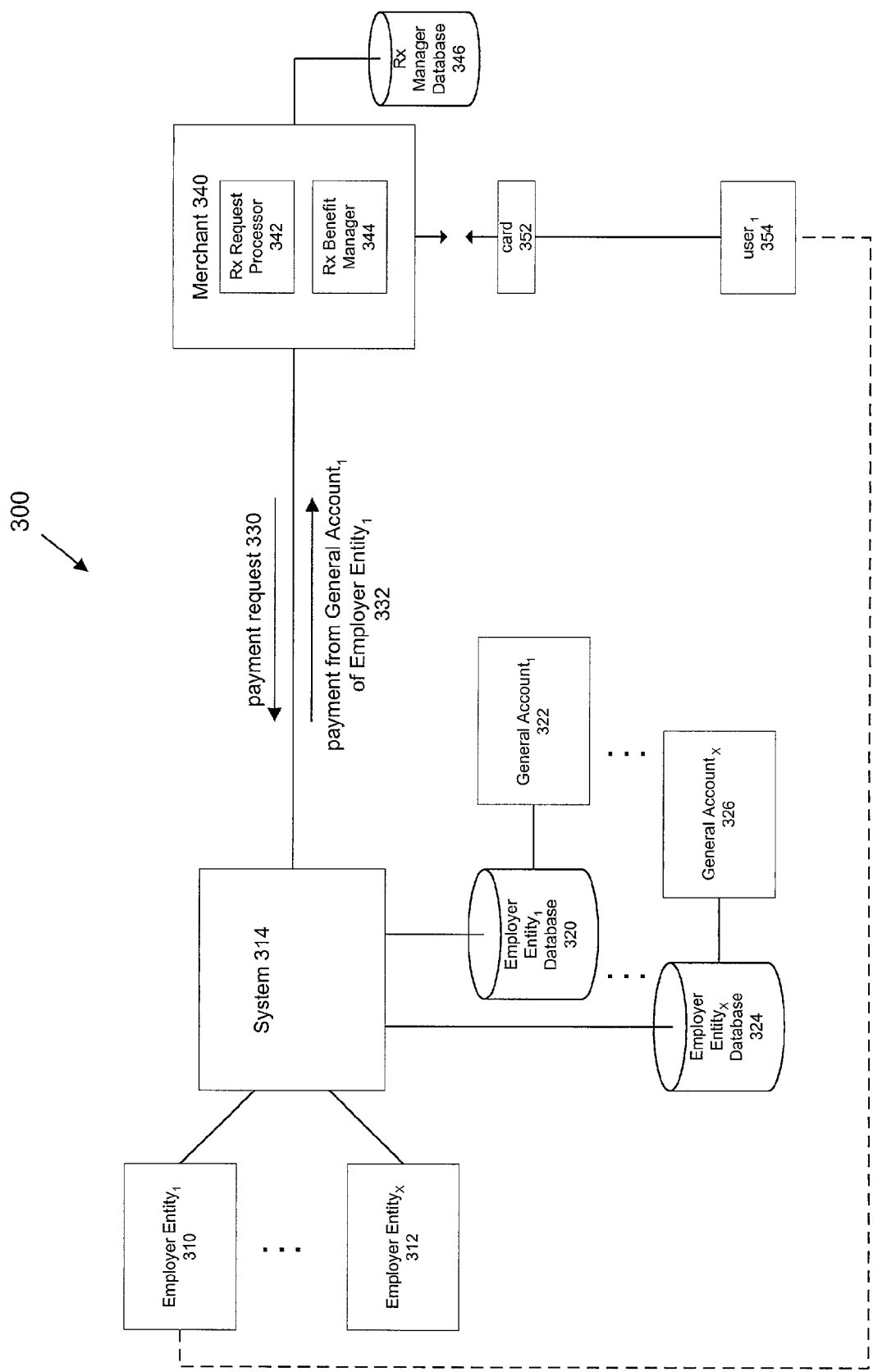
FIG. 3 is a diagram of an overall system for providing prescription drug coverage, according to an embodiment of the present invention.

FIG. 3 is a diagram of an overall system 300 for providing prescription drug coverage, according to an embodiment of the present invention. Employer Entity$_1$ 310 may register with System 314 of the present invention. Other employer entities may register with System 314, as illustrated by Employer Entity$_x$ 312. System 314 may include a database for each registered employer entity. For example, Employer Entity$_1$ Database 320 may contain information related to users associated with the Employer Entity$_1$. In addition, Employer Entity$_x$ Database 324 may contain information related to users associated with the Employer Entity$_x$. For each Employer Entity, an associated general account may be maintained through System 314. For example, General Account$_1$ 322 may be associated with Employer Entity$_1$ 310. In addition, General Account$_x$ may be associated with Employer Entity$_x$ 312. Prescription payment for a user associated with Employer Entity$_1$ may be fulfilled through General Account$_1$.

A user associated with an employer registered with the system may present an associated object to an identified merchant for prescription fulfillment and payment. For example, user$_1$ 354 may be associated (e.g., employed) by Employer Entity$_1$ 310. User$_1$ 354 may present an object associated with system 314. For example, the object may include card 352 or other identifier (e.g., identification number). User$_1$ may present card 352 for prescription fulfillment and payment to a participating Merchant 340, authorized by system 314. According to an embodiment of the present invention, card 352 may bear the name, logo, symbol and/or other identifying mark associated with Merchant 340. Thus, card 352 may be restricted for use only with Merchant 340. Other restrictions may be identified.

The point of sale transaction may occur in person, through mail order, via Internet or other modes of communication. For example, card 352 may be presented to a pharmacy associated with Merchant 340. In another example, an identification number (which may include numbers and/or letters) may be submitted when the point of sale transaction occurs via mail order, telephone, Internet or other form of communication.

As illustrated in FIG. 3, Merchant 340 and System 314 may be separate entities. In another example, Merchant 340 and System 314 may be a single unit. Other combinations and variations may be implemented.

Other restrictions to merchant channels and/or uses may be specified as well. For example, a group of merchant channels may be identified. In another example, a single merchant (or chain of merchants) may be specified. In addition, use of the card may be restricted as well. For example, the card may be used to fulfill prescriptions from physicians and/or other authorized entities. Within the prescription use, other restrictions may be applied as to what type of prescriptions may be fulfilled.

According to another embodiment of the present invention, Merchant 340 may implement prescription request processor 342, prescription benefit manager 344 and other functions. One or more databases may store information related to users, existing prescriptions, medical data and other relevant information. For example, prescription request processor 342 may receive a prescription payment request, verify price information, and send the payment request to system 314 of the present invention. In addition, a maximum spending limit may be imposed. For example, a user may be limited to $2000 (or other predetermined or variable amount) for purchasing prescriptions for a defined time period (e.g., month, 6 months, 1 year, etc.). Various safeguards may be incorporated to limit an Employer Entity's exposure (or potential liability). For example, an aggregate stop loss limit insurance policy may be implemented. Other information may be accessed and operations may be performed.

Prescription benefit manager 344 may monitor prescription data for various users. For example, prescription benefit manager 344 may verify and cross check a current prescription with possible drug interactions with other prescriptions, medications, existing conditions, etc, associated with user$_1$ 354. Other safety checks may be performed by prescription benefit manager processor 344. For example, transactional and historical data for each user may be stored and maintained in a remote or local database, as illustrated by pharmacy manager database 346. This data may be sorted and checked for various queries, such as adverse drug interaction. This data may be analyzed via other queries as well.

In another example, personalized and/or customized information may be accessed for a particular user. Relevant health information may be presented to the user based on current and past prescription transactions. For example, if a user submits prescriptions for heart medication, pharmacy benefit manager 344 may supplement the prescription with information related to healthy eating habits to reduce stress and/or other preventive information.

Discount benefits may also be realized through pharmacy benefit manager 344 where an employer or other entity may provide (or subsidize) discounted prescriptions. For example, a governmental entity may issue a prescription card to senior citizens who may receive discounts for prescriptions through the use of the prescription card. Discounts may be realized and fulfilled at the time of transaction. Other benefits may be customized and made available to users, employers and/or merchants.

When presented for prescription fulfillment and payment, Merchant 340 may collect a co-pay from the user, if applicable. A payment request 330 may be forwarded to system 314. Payment request 330 may be received and associated with the appropriate employer entity. The associated general account may then be reduced by the amount of the payment request. For example, the payment request amount may include an amount of the transaction minus a co-pay amount. Thus, payment fulfillment may be realized quickly and efficiently, as illustrated by 332.

Figure 4A:
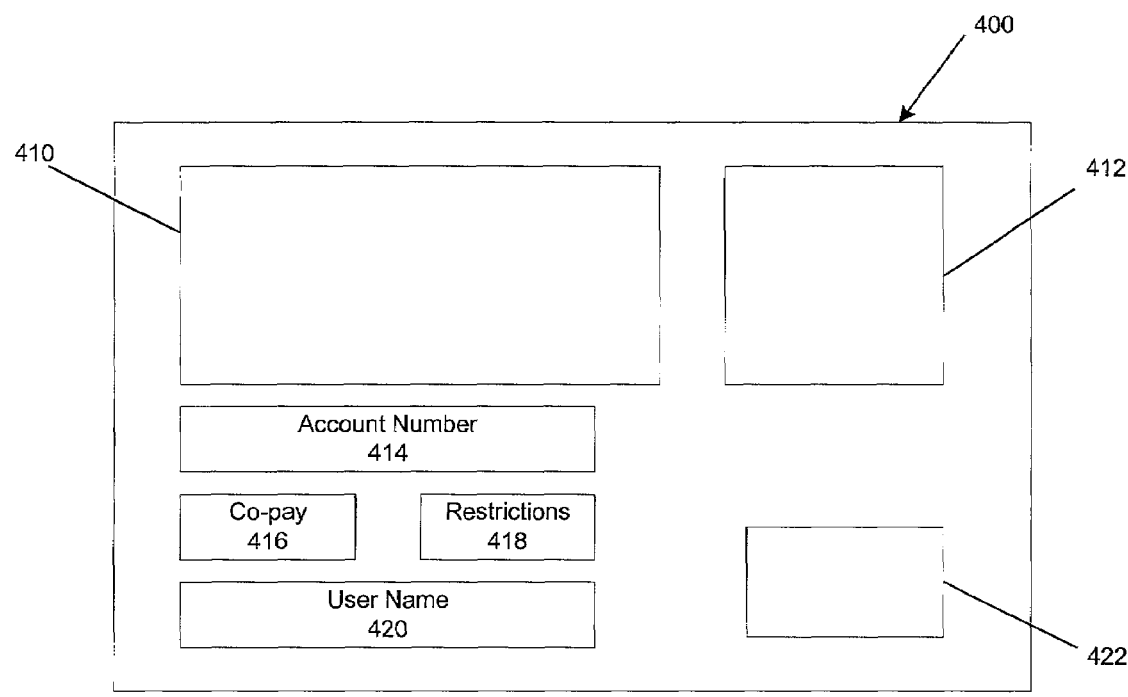
FIG. 4a is an example of a front view of a card associated with a system and process of the present invention.

FIG. 4a is an example of a front view of card, as illustrated by 400, associated with a system and process of the present invention. For example, the card may be used to receive prescriptions at authorized merchants. Other objects may be associated with the system and process of the present invention. According to an embodiment of the present invention, one or more specific merchants may be identified. For example, an exclusive merchant may provide a system and process for providing prescription drugs. As such, a logo associated with the authorizing merchant may be displayed at 410. In addition, a graphic may be displayed as well, at 412, if desired. Various types of display (e.g., color, size, font, etc.) may be displayed on the card. In another example, if a group of merchants are participants, a general logo may be displayed, as illustrated by 410. A general logo may include a general use, such as prescription card, drug card, etc.

Section 414 may present an account number associated with the user authorized to use card 400. The user name or other identifier may be displayed in section 420. In another example, an employer's name or other identifier may be displayed. If a co-pay applies, the co-pay amount may be displayed in section 416. Various restrictions may be displayed in section 418. For example, card 400 associated with the system and process of the present invention may be accepted by various credit card channels for convenience. Section 422 may display an applicable credit card channel, such as VISA, Mastercard, Discover, American Express, for example.

According to another embodiment of the present invention, a card associated with the system and process of the present invention may be a stored value card, which enables a card to be pre-loaded with value. Thus, the card may not be subject to credit restrictions and therefore may be considered less burdensome. A stored value card of the present invention may tie a card and an associated user to a general account. This feature of the present invention reduces administrative burdens, credit burdens, and manual collection inefficiencies. In addition, the card itself may not carry the value of an account. Thus, if a user misplaces or loses an associated card, the value associated with the card is not lost because the card is tied to a general account by the system of the present invention.

Figure 4B:
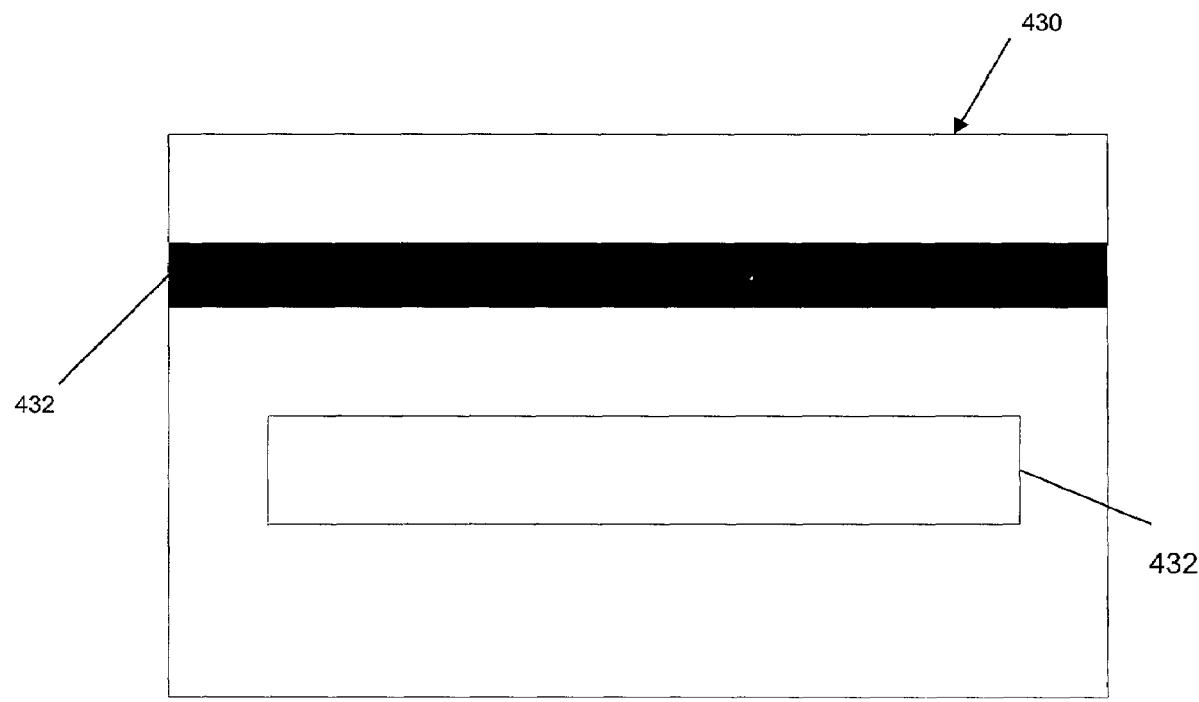
FIG. 4b is an example of a back view of a card associated with a system and process of the present invention.

FIG. 4b is an example of a back view of a card, as illustrated by 430, associated with a system and process of the present invention. 432 represents a magnetic strip that enables a card reader to access authorization information. A user's signature may be displayed in section 434. Other information may be displayed as well.

Various benefits may be realized through the present invention. For example, merchants and/or other participants may receive payment (or fulfillment) immediately or within a short period of time. A merchant entity may generate a greater volume of traffic and business through exclusive use of a prescription card, in accordance with the present invention. In addition, a merchant or other authorized entity may identify specific merchant channels and/or specific users to customize the method and system of the present invention.

Various business models may be implemented in accordance with the present invention. For example, a fee or a percentage of each transaction may be paid by a merchant entity participating with the system of the present invention. This fee may be assessed at the time of each transaction. Other arrangements may be implemented. For example, a merchant may pay a rate of a certain percentage of each transaction associated with the prescription card. For example, a merchant may agree to pay 1.60% (or other agreed percentage) of the amount of each transaction.

According to another embodiment of the present invention, the current interchange fee associated with credit payment networks may be applied. As such, the current interchange fee may be applied to a transaction price made through a system and method of the present invention. Other arrangements may be implemented.

Other embodiments, uses and advantages of the present invention will be apparent to those skilled in the art from consideration of the specification and practice of the invention disclosed herein. The specification and examples should be considered exemplary only. The intended scope of the invention is only limited by the claims appended hereto.

What is claimed is:

1. A computer implemented method for providing payment of services, comprising the steps of:
    enabling an entity to establish a general account for payment of services for a user associated with the entity through a registration means, wherein the entity is an employer offering prescription drug coverage to the user;
    identifying a merchant channel for retrieval of services through a merchant identification means, wherein the merchant channel comprises a pharmacy benefit manager for providing relevant medical information associated with the one or more services, wherein the pharmacy benefit manager detects adverse drug interactions for the user;
    identifying one or more services that are retrievable at the identified merchant channel through a service identification means, wherein the one or more services comprise prescription drug services;
    providing a stored value card product to enable the user associated with the entity for engaging in a purchase transaction with the stored value card product through the merchant channel for an identified prescription drug service where a payment request is submitted, the stored value card carries a single balance, displays a co-pay amount and identifies the merchant channel, the merchant channel comprises an exclusive merchant;
    retrieving user specific information when the stored value card product is accessed by the merchant where the merchant views the user specific information comprising a plurality of health information, personal information, customized information and historical information;
    supplementing the purchase transaction, based on the user specific information, with additional information from the merchant; and
    fulfilling the payment request from the general account wherein the general account is reduced by a purchase amount, wherein the general account is managed by the employer for a plurality of employees.

2. The method of claim 1 wherein the merchant channel is one or more retail entities comprising a pharmacy.

3. The method of claim 1 wherein the one or more services comprises prescription drug services.

4. The method of claim 1 wherein the purchase transaction occurs through one or more of mail order, Internet, and telephone.

5. The method of claim 1 wherein the purchase amount is an amount reduced by a portion of the purchase amount paid by the user.

6. The method of claim 1, wherein the general account is established for payment of services for non employees of the employer, wherein the non employees are identified by the employer has being eligible to receive health coverage from the employer.

7. The method of claim 1, where level of authorization, degree of benefit and type of coverage are identified for each user or employee.

8. A system for providing payment of services, comprising:
    registration means for enabling an entity to establish a general account for payment of services for a user associated with the entity, wherein the entity is an employer offering prescription drug coverage to the user;
    merchant identification means for identifying a merchant channel for retrieval of services, wherein the merchant channel comprises a pharmacy benefit manager for providing relevant medical information associated with the one or more services, wherein the pharmacy benefit manager detects adverse drug interactions for the user;
    service identification means for identifying one or more services that are retrievable at the identified merchant channel wherein the one or more services comprise prescription drug services;
    enabling means for providing a stored value card product enabling the user associated with the entity to engage in a purchase transaction with the stored value card product through the merchant channel for an identified prescription drug service where a payment request is submitted, the stored value card product carries a single balance, displays a co-pay amount and identifies the merchant channel, the merchant channel comprises an exclusive merchant;
    means for retrieving user specific information when the stored value card product is accessed by the merchant, the user specific information comprising a plurality of health information, personal information, customized information and historical information where the merchant supplements the purchase transaction, based on the user specific information, with additional information from the merchant; and
    fulfillment means for fulfilling the payment request from the general account wherein the general account is reduced by a purchase amount, wherein the general account is managed by the employer for a plurality of employees.

9. The system of claim 8 wherein the merchant channel is one or more retail entities comprising a pharmacy.

10. The system of claim 8 wherein the one or more services comprises prescription drug services.

11. The system of claim 8 wherein the purchase transaction occurs through one or more of mail order, Internet, and telephone.

12. The system of claim 8 wherein the purchase amount is an amount reduced by a portion of the purchase amount paid by the user.

13. The system of claim 8, wherein the general account is established for payment of services for non employees of the employer, wherein the non employees are identified by the employer has being eligible to receive health coverage from the employer.

14. The system of claim 8, where level of authorization, degree of benefit and type of coverage are identified for each user or employee.

* * * * *